United States Patent [19]

Girard

[11] 4,167,044

[45] Sep. 11, 1979

[54] MEANS FOR ACTUATING ARTIFICIAL OR DISABLED ARM MEMBERS

[75] Inventor: Leon E. Girard, Ames, Iowa

[73] Assignee: Iowa State University Research Foundation, Inc., Ames, Iowa

[21] Appl. No.: 880,367

[22] Filed: Feb. 23, 1978

[51] Int. Cl.$^2$ ............................. A61F 1/00; A61F 1/06
[52] U.S. Cl. .............................................. 3/1; 3/12.6; 3/12.7; 128/77
[58] Field of Search ................. 3/1, 1.1, 1.2, 12–12.7; 128/77

[56] References Cited

U.S. PATENT DOCUMENTS

| | | | |
|---|---|---|---|
| 1,338,155 | 4/1920 | Pringle et al. | 3/12.6 |
| 2,549,792 | 4/1951 | Fletcher | 3/12.6 |
| 2,553,277 | 5/1951 | Robinson et al. | 3/1 |
| 2,556,524 | 6/1951 | Drennon | 3/12.7 |
| 2,885,686 | 5/1959 | Giaimo | 3/1.1 |
| 3,273,169 | 9/1966 | Taylor et al. | 3/12.3 |
| 4,084,267 | 4/1978 | Zadina | 3/1.1 |

FOREIGN PATENT DOCUMENTS

7014761  4/1971  Netherlands ............................... 3/12.6

*Primary Examiner*—Ronald L. Frinks
*Attorney, Agent, or Firm*—Zarley, McKee, Thomte, Voorhees & Sease

[57] ABSTRACT

A means for actuating artificial or disabled arm members is described. The control mechanism may be either used to control the operation of an artificial hand or a prosthesis attached to a disabled arm. The prosthesis comprises a wrist-engaging portion having a rigid thumb portion extending therefrom and a finger-supporting portion also extending therefrom. The finger-supporting portion has sufficient flexural characteristics so that the supported fingers are normally held in a partially opened position. The artificial hand includes a substantially rigid thumb portion and a plurality of flexible finger members. The artificial hand is comprised of a single jointless material having springlike characteristics whereby the springlike characterstics of the hand will normally maintain the finger members in an open position relative to the thumb portion. A control apparatus is provided for controlling the operation of the fingers in both the prosthesis and artificial hand devices. A cable member extends from the finger-supporting portion of the prosthesis or the fingers of the artificial hand to a movable portion of the person's body. The control apparatus is operatively connected to the cable for opening the supported fingers, maintaining a fixed position of these supported fingers or closing the supported fingers upon the execution of a single impulse by the person.

6 Claims, 7 Drawing Figures

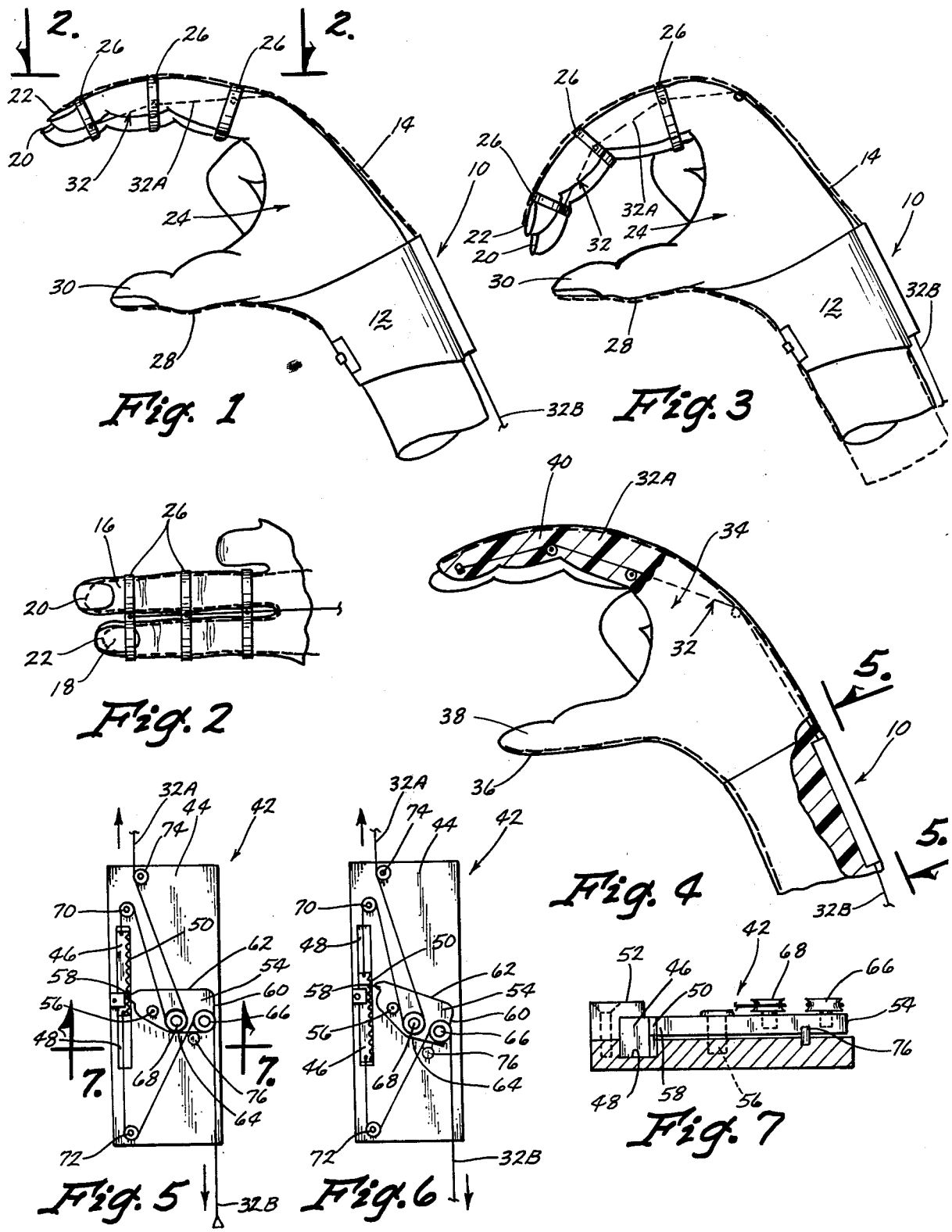

MEANS FOR ACTUATING ARTIFICIAL OR DISABLED ARM MEMBERS

BACKGROUND OF THE INVENTION

This invention relates to an improved means for controlling the operation of an artificial or disabled arm member and more particularly a means for actuating an artificial or disabled hand.

Many types of elaborate devices have been provided for actuating artificial or disabled hand members but it is believed that all of the devices require a plurality of impulses by the person to actuate the same. Typical of the prior art devices are illustrated in the following United States patents:

| Patent No. | Inventor | Date |
| --- | --- | --- |
| 1,293,478 | F. Lastawskas | 2/4/19 |
| 1,501,308 | F. Burney, Jr. | 7/15/24 |
| 2,301,009 | D. B. Becker | 11/3/42 |
| 2,500,614 | C. Lohmann | 3/14/50 |
| 2,733,545 | C. T. Guadagna | 2/7/56 |
| 2,867,819 | L. E. George | 1/13/59 |
| 1,338,155 | A. Pringle, et al | 4/27/20 |
| 1,385,669 | Otto Dilworth | 7/26/21 |
| 2,528,464 | Wilkerson, et al | 10/31/50 |
| 2,540,375 | G. M. Motis | 2/6/51 |
| 2,549,792 | M. J. Fletcher | 4/24/51 |
| 3,822,418 | Yakobson, et al | 7/9/74 |

Therefore, it is a principal object of the invention to provide an improved means for actuating artificial or disabled arm members.

A still further object of the invention is to provide an improved means for actuating artificial or disabled arm members by a single impulse on the part of the person.

A still further object of the invention is to provide an artificial hand which is comprised of a single jointless material having springlike characteristics so that the springlike characteristics of the hand will normally maintain the finger members in an opened position relative to a substantially rigid thumb portion.

A still further object of the invention is to provide a quick release mechanism for controlling the operation of artificial or disabled arm members.

A still further object of the invention is to provide a means for actuating artificial or disabled arm members which is convenient to use and is durable in use.

These and other object will be apparent to those skilled in the art.

BRIEF DESCRIPTION OF THE DRAWINGS

FIG. 1 is a side view of a prosthesis attached to a disabled hand:

FIG. 2 is a partial top view of the device of FIG. 1 as seen on lines 2—2 of FIG. 1:

FIG. 3 is a view similar to FIG. 1 except that the control mechanism has been actuated to move the fingers to a partially closed position:

FIG. 4 is a side view an artificial arm:

FIG. 5 is a plan view of the control mechanism as seen on lines 5—5 of FIG. 5:

FIG. 6 is a view similar to FIG. 5 except that the ratchet of the control mechanism has been disengaged from the gear rack; and FIG. 7 is an enlarged sectional view seen on lines 7—7 of FIG. 5.

DESCRIPTION OF THE PREFERRED EMBODIMENTS

Referring to FIGS. 1, 2 and 3, the numeral 10 refers to a prosthesis including a wrist or forearm engaging portion 12 which is adapted to embrace the forearm or wrist of the disabled arm as illustrated. The prosthesis 10 also includes a finger-supporting portion 14 extending from wrist-supporting portion 12. As seen in FIG. 2, finger-supporting portion 14 includes at least a pair of supporting members 16 and 18 which extend over fingers 20 and 22 of the person's hand which is referred to generally by the reference numeral 24 in FIG. 1. Ring-like members 26 extend between the supporting members 16 and 18 and they are adapted to have the fingers 20 and 22 extend therethrough as illustrated in the drawings.

As seen in FIG. 1, the finger-supporting portion 14 has an inherent curvature so that the fingers are held in the open position illustrated in FIG. 1 due to the inherent flexural characteristics of the finger-supporting portion 14. Preferably, the finger-supporting portion 14 as well as the prosthesis itself is constructed of a polycarbonate such as Lexan (TM). Prosthesis 10 also includes a substantially rigid thumb supporting portion 28 which is adapted to engage the thumb 30 as illustrated in FIGS. 1 and 3 to maintain the thumb 30 in position. The numeral 32 refers to a cable which is connected to the finger-supporting portion 14 as illustrated in FIGS. 1 and 3 so that pulling movement exerted on the cable 32 will cause the finger-supporting portion 14 and the fingers to be moved from the open position of FIG. 1 to the partially closed position of FIG. 3. Release of the pulling force on the cable 32 permits the finger members and the finger-supporting portion 14 to move from the position of FIG. 3 to the position of FIG. 1 due to the inherent flexural characteristics of the prosthesis.

FIG. 4 illustrates an artificial hand which is constructed of the same material as the prosthesis 10. As stated, the preferred material is a polycarbonate such as Lexan. As seen in FIG. 4, the artificial hand 34 is provided with a stiffening member 36 which is positioned in the thumb portion 38 so as to maintain the thumb portion 38 in position. A cable 32 is operatively connected to the fingers 40 as illustrated to cause the fingers to be moved to the closed position when a pulling force is exerted thereon. When the pulling force is released from the cable 32, the fingers return to the open position. It is important to note that the hand 34 is comprised of a single jointless material having springlike characteristics so that the springlike characteristics of the hand will normally maintain the finger members in the open position relative to the thumb portion.

The control mechanism for controlling the operation of the prosthesis 10 and the artificial hand 34 is illustrated in FIGS. 5-7 and is generally represented by the reference numeral 42. Control mechanism 42 generally comprises a support means 44 having a gear rack 46 longitudinally movably mounted thereon within groove 48. As seen in the drawings, gear rack 46 is provided with a plurality of teeth 50 at one side thereof. Gear rack 46 is maintained in groove 48 by keeper 52. The numeral 54 refers to a ratchet which is pivotally connected to support means 44 by pin 56. For purposes of description, ratchet 54 will be described as including ends 58 and 60 and opposite sides 62 and 64.

As seen in the drawings, end 58 of ratchet 54 is adapted to engage the teeth 50 of gear rack 46 when in the position of FIG. 5 to limit the movement of the gear rack 46. Ratchet 54 is provided with a pulley 66 rotatively mounted thereon adjacent side 64 at end 60. Ratchet 54 is also provided with a pulley 68 rotatively mounted thereon adjacent side 64 between pulley 66 and pin 56. Pulleys 70 and 72 are rotatively mounted on support means 44 adjacent the opposite ends of gear rack 46 as illustrated in FIG. 5. The numeral 74 refers to a pulley mounted on support means 44 as also illustrated in FIG. 5. Cable portion 32a extends from the finger-supporting portion 14 of the prosthesis 10 or the fingers of the artificial hand while cable portion 32b extends to a movable portion of the person's body such as a shoulder, neck, etc. As seen in FIGS. 5 and 6, cable portion 32b extends around pulley 66, then around pulley 72 and is connected to one end of the gear rack 46. Cable portion 32a has one end thereof connected to the other end of gear rack 46 and extends around pulley 70, thence around pulley 68 and thence around pulley 74. For purposes of description, cable movement in the direction of the arrow at the lower portion of FIGS. 5 and 6 will be referred to as first direction while cable movement in the direction of the arrow at the top portion of FIGS. 5 and 6 will be referred to as second direction. Generally speaking, cable movement in the first direction causes the fingers of the prosthesis or artificial hand to be moved to the closed position while movement of the cable in the second direction will cause the fingers to be moved to the open position.

Assuming that the fingers are in the position of FIG. 1, the method of closing the same is as follows. When a force is applied to the cable portion 32b in the first direction (resulting from shoulder movement or the like) the cable member 32a is also moved in the first direction so that the fingers are pulled towards to the rigidly supported thumb. Cable movement in the first direction also causes the ratchet 54 to be moved to the position of FIG. 6 so that the gear rack is free to move. At any time during the finger closing sequence, the position may be maintained by a rapid release of pulling force on cable portion 32b which causes ratchet 54 to rotate about pin 56 from the position of FIG. 6 to the position of FIG. 5 to lock gear rack 46 in position. In other words, the ratchet 54 pivotally moves to the position of FIG. 5 to lock the gear rack in position before the gear rack 46 has had an opportunity to respond to the sudden release of pulling force on the cable portion 32b.

When it is desired to return the fingers to the open position, a slight pulling force is applied in the first direction on cable 32b. The pulling action causes ratchet 54 to rotate until it engages stop 76. When stop 76 is engaged by the ratchet 54, the person slowly releases the cable portion 32b in the second direction which maintains the ratchet 54 in the position of FIG. 6 while permitting the movement of the cable member 32a in the second direction so that the fingers may open. As previously stated, the inherent flexural characteristics of the finger-supporting portion and the artificial hand provides the necessary springlike characteristics to return the fingers to the open position.

Thus it can be seen that a novel means has been provided for actuating artificial or disabled arm members which accomplishes at least all the stated objectives.

I claim:
1. In combination,
a prosthesis adapted to be secured to a person's hand, said prosthesis comprising a rigid thumb supporting portion and a flexible finger supporting portion, said finger supporting portion having a normal flexure whereby the fingers being supported thereby are normally maintained in an open position with respect to the supported thumb, an elongated flexible cable member having one end operatively secured to said finger supporting portion for moving said supported fingers towards a closed position, relative to the supported thumb, when said cable member is moved in one direction, the other end of said cable member being adapted to be operatively secured to a movable portion of the person's body, and a mechanical control operatively connected to said cable member for opening said supported fingers, maintaining a fixed position of said supported fingers and closing said supported fingers upon the execution of a single impulse by the person, said mechanical control including control means for locking said supported fingers in a fixed closed position upon a quick instantaneous release of said cable, and for releasing said supported fingers to permit said fingers to move towards an open position when said cable is slowly and gradually released.

2. The combination of claim 1 wherein said control comprises a support means, a gear rack longitudinally moved, mounted on said support means and having opposite ends, said cable member comprising a first cable portion secured to one end of said gear rack and extending to said finger supporting portion and a second cable portion secured to the other end of said gear rack and adapted to extend to said movable portion of the person's body, said gear rack having gear teeth along one side thereof, a ratchet pivotally mounted on said support means and being movable from first to second positions, said ratchet being in engagement with the teeth on said gear rack when in its said first position to limit the movement of said gear rack and said finger supporting portion, said ratchet being out of engagement with the teeth on said gear rack when in its said second position whereby said gear rack and said finger supporting portion may be moved by said movable portion of the person's body, first and second pulleys rotatably mounted on said support means at opposite ends of said gear rack, and third and fourth pulleys rotatably mounted on said ratchet, said first cable portion extending from said gear rack thence around said second pulley, thence around said fourth pulley, thence towards said prosthesis, said second cable portion extending from said gear rack, thence around said first pulley, thence around said third pulley, thence towards said movable portion of the person's body.

3. The combination of claim 2 wherein said ratchet has first and second ends and first and second sides, said ratchet having means on its said one end adjacent first side for engagement with said gear rack, the pivotal connection between said ratchet and said support means being positioned inwardly of said one end, said third pulley being positioned on said ratchet adjacent said second end at said second side, said fourth pulley being positioned adjacent said second side between said third pulley and said pivotal connection.

4. The combination of claim 3 wherein a stop means extends from said support means adjacent said second side of said ratchet and in the pivotal part of said ratchet for limiting the pivotal movement thereof.

5. An artificial hand comprising, a support arm portion, a hand member extending from said arm portion and comprising a substantially rigid thumb portion and a plurality of flexible finger members, said hand member being comprised of a single jointless material having spring-like characteristics whereby the spring-like characteristics of the hand will normally maintain said finger members in an open position relative to said thumb portion, control means operatively connected to at least some of said finger members and adapted to be connected to a movable portion of the person's body wearing said artificial hand, said control means adapted to cause said finger members to move to a closed position relative to said thumb portion upon actuation of said control means by the person's body, said control means including a control mechanism for selectively locking said finger members in a closed position relative to said thumb portion upon a quick and instantaneous release of said contol means by the person's body, and to permit said finger to move towards an open position when said control means is slowly and gradually released.

6. The device of claim 5 wherein said hand member is comprised of a polycarbonate.

* * * * *